United States Patent [19]

Lee

[11] Patent Number: 4,889,130

[45] Date of Patent: Dec. 26, 1989

[54] METHOD FOR MONITORING A SUBJECT'S HEART AND LUNG SOUNDS

[76] Inventor: Arnold St. J. Lee, 2008 Cotner Ave., Los Angeles, Calif. 90025

[21] Appl. No.: 262,052

[22] Filed: Oct. 24, 1988

Related U.S. Application Data

[60] Continuation of Ser. No. 73,648, Jul. 15, 1987, abandoned, which is a division of Ser. No. 786,746, Oct. 11, 1985, Pat. No. 4,681,098.

[51] Int. Cl.⁴ .............................................. A61B 5/02
[52] U.S. Cl. .................................... 128/670; 128/716
[58] Field of Search ................ 128/630, 670, 671, 716

[56] References Cited

U.S. PATENT DOCUMENTS

| | | | |
|---|---|---|---|
| 1,078,090 | 11/1913 | Foss | 5/81 R |
| 1,841,078 | 1/1932 | Baird et al. | 181/131 |
| 2,430,701 | 11/1947 | Bohannen . | |
| 2,751,268 | 6/1956 | Creelman | 269/328 |
| 3,268,845 | 8/1966 | Whitmore . | |
| 3,405,931 | 10/1968 | Anderson . | |
| 3,409,007 | 11/1968 | Fuller | 128/644 |
| 3,465,747 | 9/1969 | Rogallo | 128/721 |
| 3,506,985 | 4/1970 | Lang . | |
| 3,765,406 | 10/1973 | Toole et al. | 128/24 R |
| 3,830,896 | 8/1974 | Flicker et al. | 264/45.4 |
| 3,960,138 | 6/1976 | Doss et al. | 128/736 |
| 4,014,321 | 3/1977 | March | 356/39 |
| 4,066,072 | 1/1978 | Cummins | 128/671 |
| 4,272,878 | 6/1981 | Danforth | 264/222 |
| 4,320,766 | 3/1982 | Alihanka et al. | 128/671 |
| 4,347,213 | 8/1982 | Rogers, Jr. | 264/510 |
| 4,450,843 | 5/1984 | Barney et al. | 128/690 |
| 4,572,197 | 2/1986 | Moore et al. | 128/644 |
| 4,583,547 | 4/1986 | Granek et al. | 128/639 |
| 4,584,989 | 4/1986 | Stith | 128/54 |
| 4,622,185 | 11/1986 | Kostich | 264/222 |

FOREIGN PATENT DOCUMENTS 2711556  9/1978  Fed. Rep. of Germany ...... 128/670

OTHER PUBLICATIONS

"Ballistocardiography with Elimination of the Influence of the Vibration Properties of the Body", von Wittern, *Amer. Heart Journal*, vol. 46, Nov. 1953, pp. 705–714.

"The Effect of a Rigid Support on the Ultra-Low Frequency Ballistocardiogram", P. D. Verdouw et al., *Bibl. Cardiol.*, vol. 22, 1969, pp. 45–50.

*Primary Examiner*—Kyle L. Howell
*Assistant Examiner*—Randy Citrin
*Attorney, Agent, or Firm*—Spensley Horn Jubas & Lubitz

[57] ABSTRACT

Disclosed is a system, apparatus and method for gathering physiological data. Basic to the system of the present invention is a rigid body mold having preferably a negative impression of the dorsal half of the body. By connecting and/or embedding sensors to the body mold at specific locations, e.g., accelerometers, thermistors, and electrocardiogram electrodes, the sensors will be accurately and reproducibly positioned next to a specific body location each time the subject lies in the body mold. The body mold can be used to insulate the body from external motions thereby facilitating the preparation of a ballistocardiogram. The exact re-positioning of the body in the mold allows exact determination of the center of gravity in the horizontal plane of the body.

3 Claims, 3 Drawing Sheets

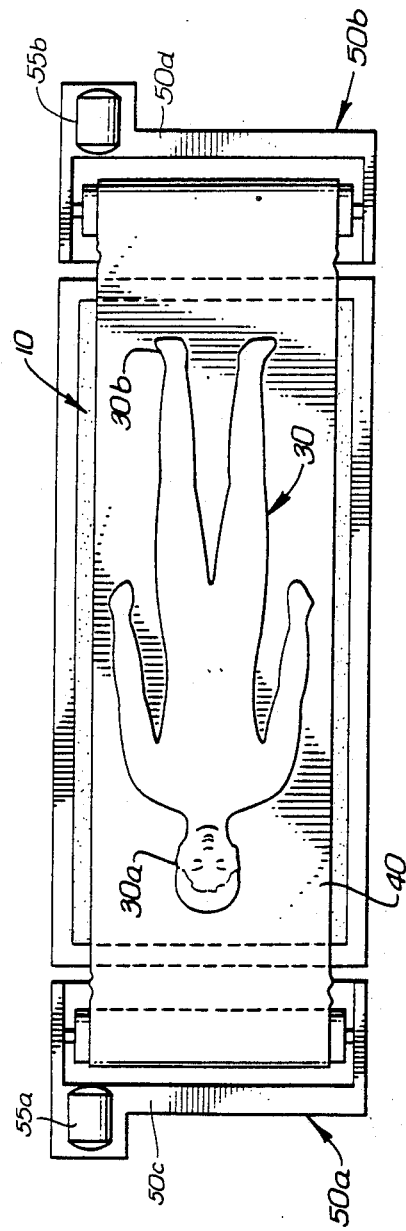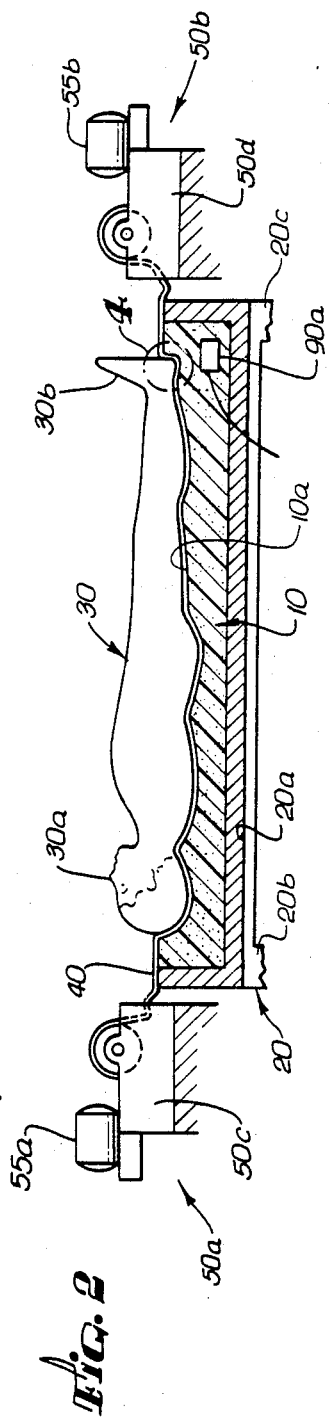
Fig. 1
Fig. 2

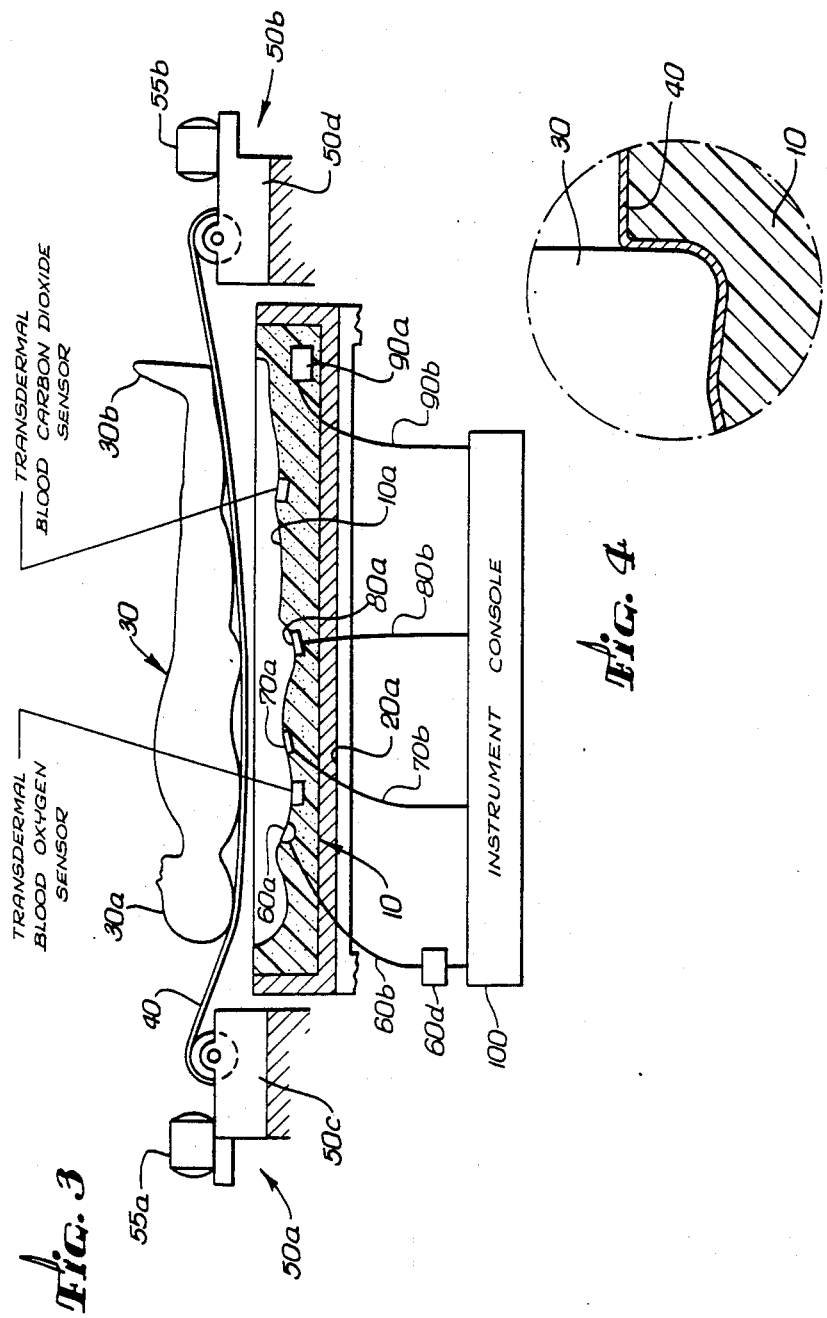

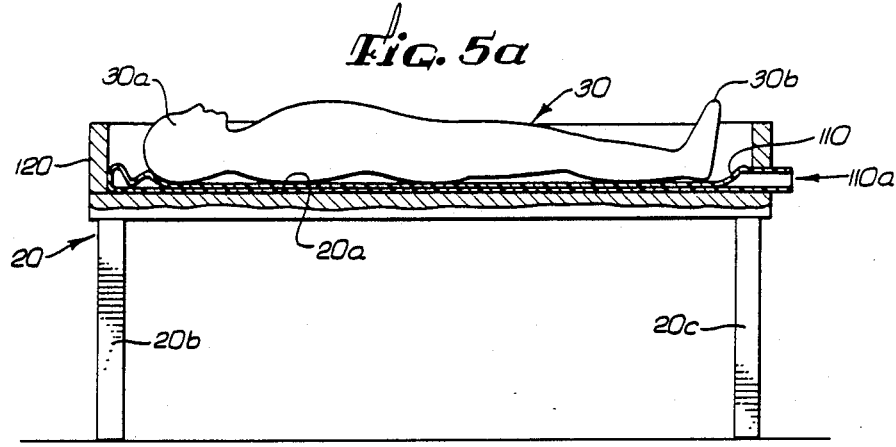
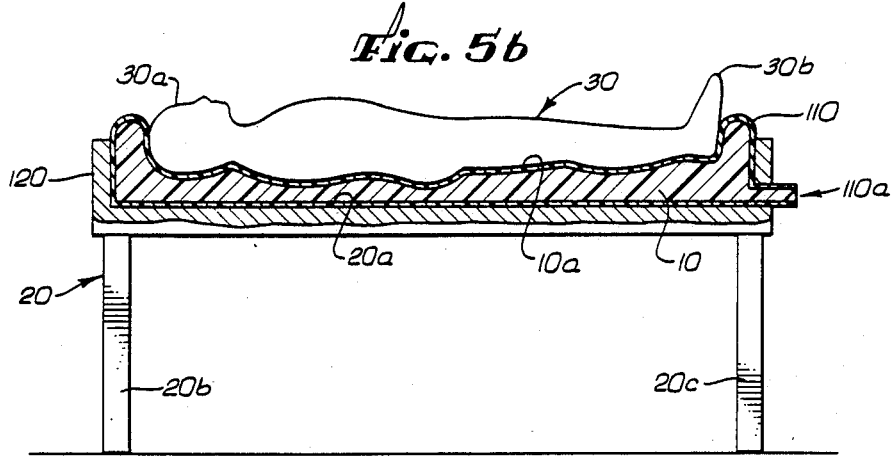
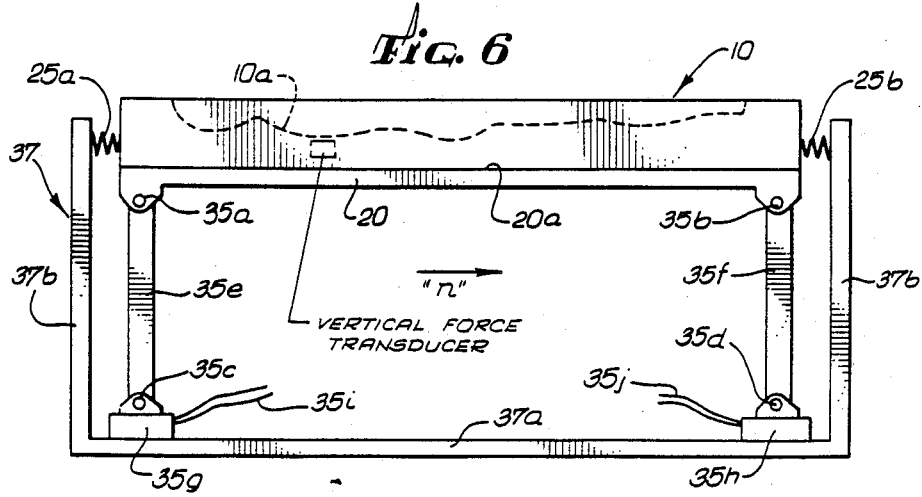

METHOD FOR MONITORING A SUBJECT'S HEART AND LUNG SOUNDS

This is a continuation of U.S. patent application Ser. No. 07/073,648 filed on July 15, 1987 now abandoned,

FIELD OF THE INVENTION

Which is a division of U.S. patent application Ser. No. 06/786,746, filed on Oct. 11, 1985 now U.S. Pat. No. 4,681,098.

FIELD OF THE INVENTION

The present invention relates to the field of medical instrumentation and methods of using such instrumentation in an accurate and reproducible manner. In particular the present invention concerns use of gravity and a body mold of a subject to facilitate use of sensors to gather physiological data.

PRIOR ART

To measure physiological conditions, electronic or other types of sensors are often used to gather desired physiological data. For example, to estimate temperature, a thermistor can be used. And to estimate the volume of blood passing through the heart in a given period of time, an accelerometer can be used. Other examples of sensors are commonly known and include without limitation an electrocardiogram electrode and a stethoscope metal bell end piece. For other examples see U.S. Pat. Nos. 3,910,257 and 4,129,125. See also Ballistocardiography and Cardiovascular Therapy, Proceedings of the Second World Congress on Ballistocardiography Cardiovascular Dynamics, Oporto 1969, pages 343-353 (New York, 1970).

To use some of the electronic sensors mentioned above, the sensor is typically strapped, suction-cupped or otherwise affixed directly to the human body at desired specific body locations. See for example U.S. Pat. No. 3,910,257. It is obviously important to firmly position the electrodes and sensors in an exact location on the patient to reduce the chances of error and to attempt to achieve reproducible results. However, due to the typical methods of sensor affixation, the data obtained is often irreproducible as it is not readily possible to locate the sensor in the same place on the body each time a test is taken. Most sensor affixation requires the services of an attendant, especially if the sensor must be applied to the patient's back. However, even if it is possible to reach the desired sensor location, the patient would have to be specially trained to apply the sensor properly. Further, in cases where the electrode is strapped to a patient, the electrode will often not stay in the same position if the patient moves.

To estimate blood flow through the heart there are basically two alternatives. In one alternative, a sensor intrusively enters the body through a vein and through the heart, thereby being a time-consuming, costly and dangerous testing procedure. The alternative method of ballistocardiography involves placing the subject on a special bed and involves using a motion transducer to measure body movement caused by the heart beat. Accurate use of a motion transducer requires that the body remain still and free from the effects of external movements such as microseisms in the ground, structural building vibrations, and dorsal tissue vibrations. However a motion transducer connected to a bed often yields data confused by spurious oscillating connections between the patient and the sensor. The prior art suggests that footboards, and lateral clamps or straps, greatly improve the coupling between the body and bed, and that the dorsal spring constant can be increased by having a rough surface on the bed so that when the subject lies on the bed with the subject's feet against a footboard and knees flexed, full extension of the legs keeps a high tension in the dorsal tissue all during data taking; however, even the better methods of ballistocardiography have not produced the reproducibility and accuracy desired. Moreover, the positioning of the patient with respect to the sensor, electrodes and ballistocardiograph bed, or the positioning of the sensors, electrodes, etc., with respect to the patient has required the services of an attendant skilled in the techniques required.

Further, the excitations of body resonances by the familiar physician's "thumping" the chest has up to this time required the active attendance and participation of a highly trained professional.

DESCRIPTION OF THE DRAWINGS

FIG. 1 is a prospective top view of a system of the present invention.

FIG. 2 is a side view of a system of the present invention with the subject's body lying in the body mold depression of the present invention.

FIG. 3 is the same view as FIG. 2 with the subject's body raised out of the body mold depression of the present invention.

FIG. 4 is an enlarged view of a portion of FIG. 3 showing a body/hammock/body mold sandwich.

FIGS. 5a,b shows the body mold bag of the present invention.

FIG. 6 shows a cross-sectional diagram of the body mold of the present invention supported by vertical legs.

SUMMARY OF THE INVENTION

In its broadest sense, the present invention comprises a physiological information gathering system. The system can be particularly adapted to provide a method of in-home, self monitorization for elderly, sickly and health-concerned persons without the assistance or required presence of an attendant.

Basic to the system of the present invention is an individually made rigid body mold having a negative impression of the lower half of the body when the body is in a supine position (a depression intimately matching the dorsal half of the body). The body is confined by the body mold and is held inside it by gravity. In addition to insulating the body from the effects of external movements, the body mold also accurately and reproducibly positions the body and keeps the body stationary. By embedding or connecting sensors to the body mold at specific locations, the sensors will also be accurately and reproducibly positioned next to a specific body location each time the subject lies in the body mold. As a result, the data gathered by the sensors will provide accurate and reproducible measurements of physiological conditions. Means also are provided for conveniently moving a subject's body into and out of the body mold depression. The system overall provides significant advances in some analytical fields such as ballistocardiography, and in many fields, provides a superior method of reproducibly and accurately gathering physiological data.

DETAILED DESCRIPTION OF THE DRAWINGS

The following description is the best presently contemplated mode of carrying out the invention. This description is made for the purpose of illustrating the general principles of the invention and is not to be taken in a limiting sense. The scope of the invention is best determined by reference to the appended claims.

In general, the present invention comprises a system, apparatus and method for gathering physiological data to provide useful physiological information to the health conscious. In one embodiment of the invention, and with reference to FIGS. 1-4, the system of the present invention includes body mold 10 resting on table 20 having flat, planer upper surface 20a and preferably with four vertical table supports 20b,c (two are not shown) extending from each corner of the table. The dorsal half of a body 30 is shown lying in a negative impression 10a of the body mold 10. Sandwiched between the body 30 and the depression surface is resilient hammock 40. Extending from the top of the table 20, adjacent the head 30a and feet 30b of the body 30, are motorized hammock roller mechanisms 50a,b. The hammock 40 and the roller mechanisms 50a,b function to lift the body 30 out of, and place the body into, body mold depression 10a by making the hammock 40 rigid and flaccid, respectively. Extending from the body mold 10 are connections 60b, 70b, 80b, and 90b coupling sensors 60a (the metal bell endpiece of a stethoscope), 70a (electrocardiogram electrode), 80a (thermistor) and 90a (accelerometer) (which are embedded in the body mold 10 adjacent specific locations on the body) with instruments contained in console 100.

The body mold 10 can be made of any firm, structurally rigid material, such as a polyurethane isocyanate foaming plastic system. If used for ballistocardiography, the body mold 10 is preferably made of a low density, high modulus, foaming plastic such as that sold under the trademark "Structural Rigid Foam" by Polymer Development Laboratories, Inc. The foaming plastic is preferred due to its lightness, its low thermal conductivity and stiffness.

The body mold 10 can be individually prepared in a variety of ways; however, one way is preferred. With reference to FIGS. 5a,b, a thin plastic or rubber bag 110 having an opening 110a is placed within a mold form 120 (which is removed after mold is made) on a flat surface such as that of the upper surface 20a of the table 20. Bag opening 110a is adapted to receive nozzle (not shown) of mixing injection pump machine (not shown). Body 30 lies in a supine position on uninflated bag 110. The bag 110 is then injected with a foaming plastic mixture thereby simultaneously raising the patient off of the flat table and creating a depression 110a. By filling the bag about one-half the way up the body width, and allowing the foaming plastic or rubber to solidify, removal of the bag followed by trimming of the rough body mold will reveal the finished body mold 10. Generally, the low density foam is quick-setting. Some foaming plastics form an integral skin which results in the body mold having a tough, outer skin. Alternatively, the addition of an epoxy coat to the body mold strengthens the body mold surface.

Another way of preparing the body mold 10 involves cutting the dorsal impression from a solid plastic foam block. Optical sensor systems are available to generate a graphical representation of the subject's body which can be used to properly cut out the dorsal impression. However, since the graphical representation does not include the effects of gravity on the dorsal tissue, it is not a preferred method.

After the body mold is prepared, or in some cases as discussed below during mold preparation, sensors are connected to the mold such that their placement, coupled with the force of gravity exerted by the body when the body is in the mold depression, connects the sensors adjacent to specific body locations. Such a sensor is thereby placed in operational contact with the body portion. In appropriate cases, the sensors can be made flush with or slightly protruding from the mold by methods well known.

A variety of sensors may be connected to or otherwise embedded in the body mold 10. For example, stethoscope 60 having metal bell end piece 60a, can be, alone or together with microphone 60d or a thumper, embedded in mold 10.

The stethoscope metal bell end piece can be countersunk into the mold 10, with it preferably slightly protruding. The stethoscope can be mounted by drilling a hole having a diameter slightly larger than the sensor using a rotary tool having course burr, and countersinking the metal bell. Alternatively, the stethoscope bell can be taped to the body when the body mold is being prepared thereby simultaneously generating an impression for the stethoscope metal bell. Stethoscope 60 can be listened to via earphones (not shown) or the data received by it can be fed to an electronic microphone and amplifier coupled to the console 100. And, by listening to the stethoscope bell sounds in response to each activation of the thumper, body resonances can be determined.

As discussed below, other sensors can be embedded the same way or taped to the body during molding such as an electrocardiogram electrode 70 for determining a subjects heart rate by analyzing the amplified electrode voltage of the electrocardiogram electrodes, a thermistor or temperature transducer 80 for estimating temperature by recording the voltage output of the temperature transducer, and an accelerometer 90 as discussed in detail below. Other electrodes and sensors include impedance pneumography electrodes which are used to measure respiration frequency and crude depth of respiration, skin color sensors or transducers which can be placed adjacent specific body locations to determine oxygen saturation of the hemoglobin, pneumocardiogram electrodes, vertical force transducers, transdermal blood oxygen sensors and transdermal blood carbon dioxide sensors for estimating blood oxygen and carbon dioxide tension, respectively, heart and lung sound sensors, and lung resonance sensors.

With reference to FIG. 6 the body mold can also be used to estimate both the weight and the center of gravity of the patient by placing an appropriate sensor and amplifier on each of the vertical supports on the bed, and computer-solving the appropriate equations. Specifically, body mold 10 is firmly affixed to table or bed 20 which is connected by springs 25a,b to rigid frame 35. The bed 20 is connected by low friction axles 35a,b,c,d to rigid vertical supports 35e,f which are in turn connected to pedestals 35g,h, each having a weight or vertical force transducer (not shown) including a preamplifier. It should be appreciated that only two vertical supports are shown, but that there are four identical ones in total, one connected to each of the four corner areas of the bed. The signals from the transducer are fed via wires 35*i,j* to a console for analysis by an appropriate computer. It should also be appreciated that the bed vertical supports are wide in the perpendicular (horizontal) direction so as to facilitate restraining the bed so that it cannot move sideways.

In the art of ballistocardiography, the slight movement of the body is measured as the body reacts to the blood inertia forces caused by the heartbeat. A motion transducer or more specifically an accelerometer may be used to generate a ballistocardiogram which is basically a time-based chart of body acceleration, velocity or position data. Recordation of such data into chart form enables one to estimate the heart action and heart output of a patient relative to a previously recorded "baseline".

In the preferred method where ballistocardiography is included, an accelerometer is embedded in the body mold so that its longitudinal axis is along the longitudinal axis of the body. This is done by making a hole in the mold, inserting the accelerometer, and gluing the accelerometer to the mold. The mold will move in response to the heartbeat, and the longitudinal vibrations will be recorded by the accelerometer. By embedding the accelerometer 90*a* in the body mold 10, a ballistocardiogram sensor is accurately placed with respect to specific body portions; the body mold keeping the body still and free of the effects of its own oscillations vs. the bed and external movements. As a result, reproducible data can be obtained and accurate comparison with previous data performed.

To obtain a ballistocardiogram, the body mold may rest upon extremely slippery horizontal linear bearings, or rest upon vertical legs (see FIG. 6), in each case constraining the body mold so that it can only move in the longitudinal direction "n".

The system of the present invention is particularly useful to the elderly and invalid. The system can include a transfer mechanism to enable conveniently transferring the body 30 into and out of the body mold 10. The transfer mechanism includes head roller mechanisms 50*a*, foot roller mechanisms 50*b*, supports 50*c* and *d*, and rollable hammock 40 having one end connected to roller mechanism 50*a* and the other end connected to roller mechanism 50*b*. A motor drive 55*a,b* is provided for the head roller and the foot roller, respectively. The hammock can be made of a cloth sheet or membrane, for example, a nylon knitted fabric which is silky, flexible, thin and relatively non-distensible longitudinally. The hammock contains reinforced holes positioned to allow the electrodes and sensors to contact the skin.

While the body mold is being used, the motors are not activated thereby maintaining the hammock flaccid. The hammock therefore does not significantly effect the contours of the body mold depression. When the motors are forwardly activated, the hammock is tightened. At that point, the subject merely lies down on the hammock. The motors are then operated slowly in reverse to render the hammock flaccid thereby simultaneously placing the body into the depression. After testing is complete, the motors are again forwardly activated to render the hammock taut. The subject can then easily get off of the hammock. Compare the hammock depicted in FIGS. 2 and 3.

There are a wide variety of variations of the above description which those of skill in the art will recognize as being within the scope of the present invention. For example, the present invention, in one aspect, contemplates a revolution in medical technology. Specifically, the present invention envisions accurate in-home self-monitorization. That is, the body mold "bed" is relatively inexpensive, and can be kept in the home of any person, for example, the elderly and sickly, and used to obtain, as well as transmit, vital sign data to a physician, without the assistance of another person.

I claim:

1. A method for monitoring a subject's heart and lung sounds comprising the steps of:
   providing a rigid body mold having an impression intimately matching the entire length of the dorsal portion of the subject's body and embedding in the mold sensor means for obtaining heart and lung sounds and producing an output corresponding to such sounds;
   placing the subject in a supine position in the body mold so that the subject's heart and lung sounds can be received by the sensor means, whereby the subject's body comes into contact with said sensor means; and
   checking the resulting sensor output.

2. The method of claim 1 wherein said step of placing comprises frrst placing the subject on a thin, flexible sheet, and then lowering the sheet bearing the subject into the impression, whereby the subject's body comes into contact with said sensor means through said sheet.

3. The method of claim 1 further comprising the step of listening to the sensor output.

* * * * *